(12) United States Patent
Dadlani Dadlani et al.

(10) Patent No.: US 10,012,584 B2
(45) Date of Patent: Jul. 3, 2018

(54) SYSTEM AND METHOD FOR DETERMINING SOLUTE CONCENTRATION IN A COLORED LIQUID SAMPLE

(71) Applicant: LAB4U INC, San Francisco, CA (US)

(72) Inventors: Komal Dadlani Dadlani, Las Condes (CL); Isidro Nicolas Lagos Chavez, Santiago Centro (CL); Ivan Rodrigo Toledo Ivanovic, Providencia (CL); Ignacio Antonio Brescia Rivera, Las Condes (CL); Alvaro Jose Peralta Ocampo, Santiago Centro (CL)

( * ) Notice: Subject to any disclaimer, the term of this patent is extended or adjusted under 35 U.S.C. 154(b) by 0 days.

(21) Appl. No.: 15/125,520

(22) PCT Filed: Apr. 28, 2015

(86) PCT No.: PCT/CL2015/000030
§ 371 (c)(1),
(2) Date: Sep. 12, 2016

(87) PCT Pub. No.: WO2015/164991
PCT Pub. Date: Nov. 5, 2015

(65) Prior Publication Data
US 2017/0074783 A1 Mar. 16, 2017

(30) Foreign Application Priority Data
Apr. 30, 2014 (CL) .................................. 1150-2014

(51) Int. Cl.
*G01N 21/25* (2006.01)
*G01N 21/27* (2006.01)
*G01C 21/00* (2006.01)

(52) U.S. Cl.
CPC .............. *G01N 21/27* (2013.01); *G01C 21/00* (2013.01); *G01N 21/251* (2013.01); *G01N 21/255* (2013.01)

(58) Field of Classification Search
CPC ........ G01N 21/27; G01N 21/25; G01N 21/64; G01J 3/50; G01J 3/46; G01J 3/44
See application file for complete search history.

(56) References Cited

U.S. PATENT DOCUMENTS 5,960,104 A * 9/1999 Conners ............. G01N 21/8986
144/402
2008/0273787 A1* 11/2008 Ducksbury ........... G06T 7/0012
382/133

(Continued)

FOREIGN PATENT DOCUMENTS

WO    WO 2012/032171 A1 *  3/2012

OTHER PUBLICATIONS

International Search Report and Written Opinion in related International patent application No. PCT/CL2015/000030, dated Oct. 23, 2015, 8 pages.

*Primary Examiner* — Abdullahi Nur
(74) *Attorney, Agent, or Firm* — Law Office of Jeff Williams; J. Oliver Williams

(57) ABSTRACT

The present invention relates to a method and system, particularly a mobile device, configured for determining the solute concentrations in a colored liquid sample, which is based on imaging of the sample and standards of known concentrations of solute, and determining the concentration of the sample on the basis of processing the images and the color values that they provide.

10 Claims, 3 Drawing Sheets

(56) References Cited

U.S. PATENT DOCUMENTS

2008/0298722 A1* 12/2008 Lee .................. H04N 9/64
382/300
2009/0324036 A1* 12/2009 Batistoni ............. G01N 21/253
382/128

* cited by examiner

SYSTEM AND METHOD FOR DETERMINING SOLUTE CONCENTRATION IN A COLORED LIQUID SAMPLE

TECHNICAL FIELD

The present invention relates to the field of spectrophotometry of visible absorption, providing a method and system, particularly a mobile device, configured for determining the solute concentration in a liquid colored sample, which is based on obtaining images from a sample and from standards of known concentrations of solute, thus determining the concentration of the sample by processing the images and the color values that they provide.

BACKGROUND

Optical-chemical analyzes are the most common methods for determining the concentration of a solute in a solution, based on the ability of compounds to absorb or emit light energy of different wavelengths. Initially, visual colorimetry was used to compare the light emerging from a solution of an unknown concentration and the light emerging from a reference solution, until on the eyes of the observer, both emerging lights were identical (Garrigós L. and other. "Colorimeters" Universitat Politècnica de València. 2001). However, these results were subjective and inaccurate. Later in time, photocolorimeters were created, which consisted in a tungsten lamp where the light passed through a slit and then condenser lens, in order to obtain a parallel light beam incident on the unknown solution. Then, the lengths of the unabsorbed waves pass through a filter with a complementary color to the test solution, giving a monochromatic light. This light beam enters a photocell generating a small electrical current that increases through an amplifier, which signal is detected by a galvanometer delivering absorbance measurements. If a calibration curve is performed with standards or reference solutions, whose concentrations are known, versus the absorbance of each of them, one can determine the concentration of the solution by obtaining the absorbance. This technique is only useful when the solutions are colored, but other solutions which absorb in the range of ultraviolet light cannot be analyzed by a colorimeter. For the latter, a spectrophotometer that is capable of evaluating the absorption throughout the all UV/visible range is used. Furthermore, this equipment can distinguish between two compounds with a similar absorption, delivering absorption spectra that even allow the identification of the compounds that are being analyzed.

However, all these techniques require large and expensive equipment, so that the analysis of samples must be performed within a laboratory facility, impeding in-situ analyzes. To overcome these limitations, innovations have emerged that allow analysis of absorbance with camera phones, such as described by Z. Smith (Smith Z. et al. "Cell-Phone-Based Platform for Biomedical Device Development and Education Applications" PLoS One. 2011; 6(3): e17150), in which a grid and a collimator were attached to a cell phone camera generating an equipment sensitive to visible light between 350-650 nm. In another invention, Zhang J. (U.S. Pat. No. 8,537,343 B2) reduced the optics of the spectrometer, achieving a compact spectrometer of a wider range of light (UV, visible or infrared) which can be integrated into a cell phone or a portable electronic apparatus. Likewise, Wang S. (U.S. Pat. No. 7,420,663 B2) designed a device which is capable of measuring optical spectra, this device contains a laser or LED light source and a filtering element for a particular wavelength, which is detected and measured by a cell phone camera and the results are sent by a wireless network to a central control. There are also simpler inventions in applications that only analyze colored solutions, by impinging a light beam on the sample and obtaining a color numerical value or concentration. Such is the case of the invention of Thonhauser C. (U.S. Pat. No. 8,493,441 B2) which is a color sensing device attached to a portable electronic device that is configured to calculate the average values of discrete colors red, green and blue (RGB, red, green, blue) color processing in 8-bits per channel. This device requires that the sample is exposed to a light beam and detects the emitted wavelengths in the range of 400-700 nm. All mentioned inventions have the problem that they require an external device to the portable electronic apparatus for its use, which increases the cost of technologies and their access.

The present invention provides a practical and fast solution for analyzing concentrations of solutes in colored liquid solutions only using the integrated camera of a portable electronic device and configuring it to calculate the unknown concentration from the color evaluation of colored liquid samples whose concentrations are known, without the need to require an external measuring apparatus. This application can be useful for teaching basic concepts of chemical analysis in educational establishments, requiring only smartphone or tablet type devices, which are used by millions of people worldwide. The system calculates the concentration of a solute in a liquid solution from colored imaging which includes a calibration curve with known concentrations of liquid solutions and the sample or problem solution.

SUMMARY OF THE INVENTION

One object of the present invention is a system for determining the concentration of a solute in a colored liquid solution, said system comprising:
  a mobile device with a built-in camera;
  a screen for displaying the image;
  a memory for storing data;
  a computer application stored in the memory which performs a comparison between a colored liquid sample whose solute concentration is to be determined with respect to a plurality of solutions of known concentrations of said solute, generating images from the numerical values related to the color sample and the color of solutions of known concentrations of solute, wherein from said comparison of numerical values the solute concentration in the sample is determined; and
  a processor operatively coupled to said camera, display and memory, for executing said computer application.

The system can be implemented using any computing device from a smartphone or any portable device with internal camera.

The invention also includes a method for determining the concentration of a solute in a colored liquid solution, which is conducted through the following steps:
  placing at least 3 droplets of colored solutions of known concentration of solute on a suitable surface and under certain conditions, and at least one droplet of the sample whose solute concentration is to be determined;
  under proper conditions, capturing at least one image of the plurality of droplets with a camera coupled to a computing device, which are stored in the device memory;

entering in the memory of the device the concentration values for each of the droplets of colored solutions of known concentrations of solute;

a computer application processes the values thus obtained images of said plurality of droplets of colored solutions of known concentrations of solute and the droplet of the sample whose solute concentration is to be determined; and obtaining the value of the solute concentration of the sample on the computing device screen, calculated by the computer application.

In the first step, the droplets of colored solutions of known concentrations of solute are placed and at least one droplet of the sample whose solute concentration is to be determined on a uniform surface of contrasting color to the color of the droplets of the solutions, preferably a surface white and completely horizontal. The volume to be used may be between 15 µL and 100 µL, preferably using a volume of 30 µL. The volume and the distance between the droplets should be similar.

For capturing images of the plurality of droplets, a portable computing device containing an imaging system at a distance and at such an angle that covers all the droplets placed in that surface is required. The brightness of the area where images are captured must be uniform, from a source of natural or artificial light.

For processing the images of the droplets of colored solution of known and unknown concentrations, the computer application performs the following operations:

recognition of each droplet in at least one image previously captured, both of the plurality of droplets of colored solutions of known concentration as well as of the droplet whose solute concentration is desired to calculate;

pre-processing the image previously captured and detected in a matrix of pixels by a suitable method to eliminate the image noise;

transforming the matrix of pixels in the RGB color space to a suitable color space to isolate the sample from the rest of the image;

post-processing of previously captured image selected blocks of pixels representing a droplet on the matrix;

eliminating blocks of pixels of less than 50% larger block size;

generating a histogram of the color values of the pixels to provide color that is repeated in every droplet;

from said histogram, generating a color calibration chart versus the concentration of the droplets of colored solutions of known concentrations of solute; and calculating the solute concentration of the sample droplet whose concentration is to be determined.

The pre-processing of the image by the computer application consists in obtaining an approximation of the area of the droplets, detecting the area thereof in a matrix of pixels in the RGB color space of 16 or 24 bits, and applying a Gaussian filter image interpolation.

The post-processing of previously captured image that selects blocks of pixels representing a droplet on the matrix consists in removing those pixels whose colors do not correspond to the main recognized in every droplet, and detecting and storing into the memory the blocks of pixels on the matrix.

DETAILED DESCRIPTION OF THE INVENTION

The present invention essentially relates to a system and method that use a computer application that can be run on mobile devices and related apparatus, which allows image processing by determining the concentration of a solute in a liquid colored sample, using a plurality of reference solutions of known concentrations of solute.

Since mobile devices are currently used by millions of people in the world, the purpose of the present invention is to provide the general population with an application of easy use, with no need of using laboratory complex instrumental, and from which images of the solutions are used to evaluate and compare the color of these test solutions in relation to known concentrations of solute, thus one can determine the solute concentration in these test solutions, thereby providing a method and means for its much simpler execution in comparison with those known so far for this purpose.

The present invention therefore becomes a useful tool for determining concentrations of solute in colored liquid solutions, in places inaccessible to laboratory complex instrumental. This invention allows, for example, providing a solution for educational classrooms requiring practical teaching cases, or those requiring analyzing samples on site, outside of the laboratory facilities. Furthermore, the system and method proposed are an economic and easy technical solution compared to the use of known spectrophotometric equipment of high cost, and has the additional advantage that requires no external devices to the computational device.

The system of the present invention includes an application that performs a series of operations for obtaining the solute concentration of a sample from an image obtained by the inner camera of a computational device and the processing of said image. First, there must be a series of solutions of known concentration for the user, for generating a calibration plot with the computer application. A plurality of droplets of these solutions of known concentrations must be placed on a suitable surface and under appropriate conditions. Such suitable conditions include the use of at least three droplets of the solutions of known concentration of a similar volume.

Figure 1:
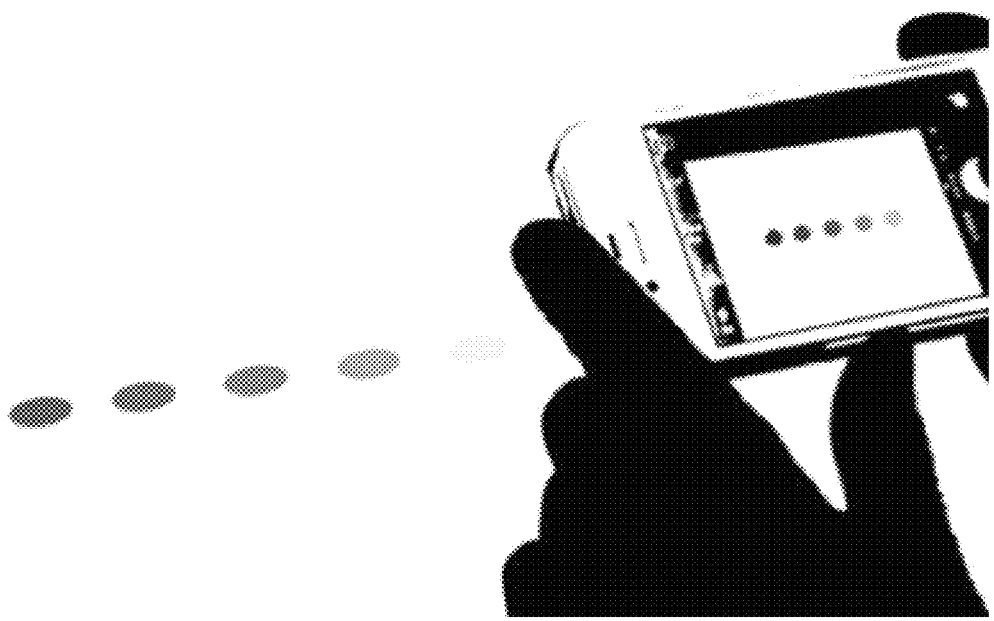
FIG. 1 is an example of the plurality of droplets under appropriate conditions placed on a suitable surface.

A non-limiting example is shown in FIG. 1, where preferably 5 droplets of 30 µL each are placed on an even surface of contrasting color to the color of the droplets, preferably a white surface. The spatial distribution of the droplets on the surface of known concentration is not relevant and has no influence on the result to obtain the solute concentration of the sample, but preferably the droplets should be arranged linearly and so decreasing in concentration, as shown in FIG. 1. Also, at least 1 droplet of the sample whose solute concentration is to be determined is placed under the same conditions as for the droplets of solutions of known concentration.

The computer application of the present invention can be installed and stored in the memory of a computing device with internal camera. A non-limiting example according to the invention of a smartphone is an iPhone 4S® by Apple Inc (1) and shown in FIG. 2. It has a camera for imaging (lens 2) and a screen 3 which displays images and serves to focus the plurality of droplets placed on a suitable surface 4, a memory for storing the computer application and the obtained images, and a processor executing the application to obtain the value of the solute concentration in the sample, by processing images from the sample and from the solutions of known concentrations.

Figure 2:
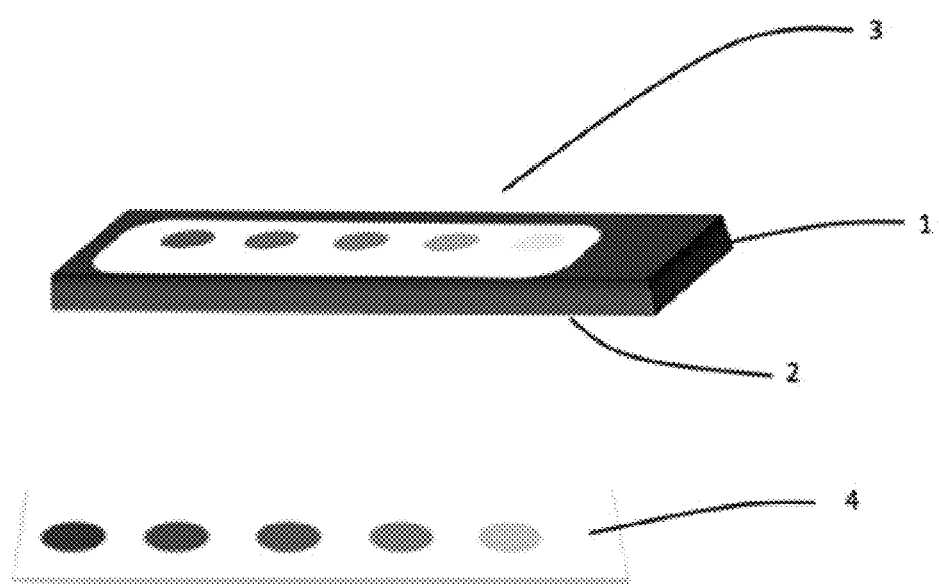
FIG. 2 is an example of using the device where the view is shown at 45 degrees smartphone on the plurality of droplets of colored solutions of known concentrations of solute at a distance such that it covers all the droplets on the intelligent phone screen.

In FIG. 2, is represented how the device camera is activated and how is displayed on the screen 3 the image output. With the camera of the mobile device the plurality of droplets is focused at an angle and appropriate distance so that all droplets are contained in the image on the screen, even illumination provided by a source of natural light, for example, near a window or outside of an establishment, or by floodlit, bulbs, lights or the camera flash, and images, which are stored in the memory of the electronic device, are captured. The plurality of droplets can be captured in a single image containing droplets of known concentration and the droplet of the sample whose solute concentration is to be determined, or alternatively it is possible to capture more than one image, first from solutions of known concentration, and then a second image from the droplet of the sample whose solute concentration is to be determined.

The computer application allows users to use an image previously stored in the memory of the computing device, or take a picture with the camera on the spot image.

Figure 3:
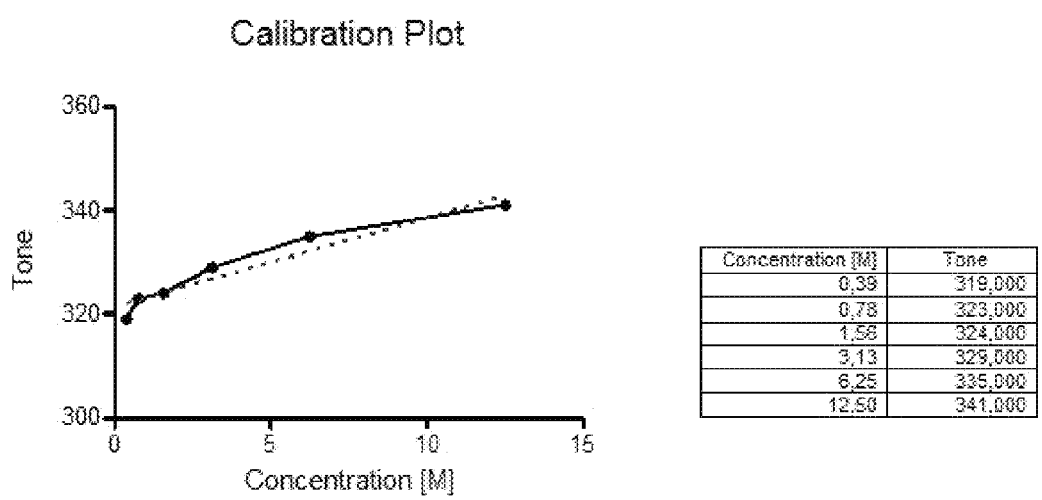
FIG. 3 is an example of the calibration curve obtained from the introduction of the concentration values of the solutions of known concentrations of solute vs tone thereof.

The application displays on screen options of "CALIBRATE" or "MEASURE", being first selected the option "CALIBRATE". About the captured image, the application identifies the droplets of known concentrations, gives them a numerical value according to the number of droplets identified in the image. The user enters values for each solution of known concentration, and the application displays on the screen of the device a table with color values of each droplet, preferably those values related to the color space HSV (hue, saturation, value) of hue, saturation and value. The application saves the concentration values entered into the memory, processes the data and stores in memory a calibration curve of concentration versus tone. Then, the user selects the option "MEASURE" and chooses a previously captured image containing the droplet of the sample whose solute concentration is to be determined or captures the image with the camera at that moment. The computer application detects the area of the droplet of the sample, the color values obtained, for instance HSV values of hue, saturation, and color value of the droplet, and compares these values to the calibration curve previously stored, obtaining the solute concentration of the sample, which is shown on the display of computing device (FIG. 3).

The captured image requires internal processing by the computer application for obtaining the color values, for which executes a pre-processing of the image, where an approximation of the area of each droplet is obtained and detects the image in a matrix of pixels in the RGB color space to 16 or 24 bits, which applies a Gaussian interpolation filter to remove background noise from the image. The application transforms the matrix of pixels RGB color space to a suitable color space, preferably to the HSV color space hue, saturation and value.

The application detects and stores in memory blocks pixels representing the droplet on the matrix, and removes those pixels whose colors do not match the primary colors recognized by the application in every droplet. Then, removes those pixels of groups of less than 50% larger block size to avoid recognizing pixels blocks spots corresponding to background noise rather than droplets. The application generates a histogram of the color values of the pixels, particularly tone value to determine the tone that is repeated in every droplet.

Using this value and the concentration values entered by the user, the application performs the calibration curve of concentration versus tone. Then, the application detects the droplet of the sample solute whose concentration is to be determined, carries out the same image processing performed previously mentioned and compares the tone value of the sample droplet with the ones of the calibration plot.

Finally, the solute concentration value of the sample, which is shown on the display of computing device is obtained.

Thus, with the simple use of a mobile electronic device can easily determine the solute concentration in a colored sample using the system and method proposed by the present invention.

The invention claimed is:

1. A system for determining the concentration of a solute in a colored liquid solution, comprising:
   a device or camera for capturing images;
   a screen for displaying the images captured by said device or camera;
   a memory for storing data;
   a computer application stored in said memory; and
   a processor operatively coupled to said device or camera, to said screen and to said memory, for executing said computer application,
   wherein said computer application performs the following operations:
   i. recognizing and detecting, in any position of a captured image, a droplet of a colored liquid sample whose solute concentration is to be determined;
   ii. obtaining numerical values related to the color of said recognized and detected image of said droplet of the sample whose solute concentration is to be determined;
   iii. comparing said obtained numerical values to a calibration curve of said numerical value as a function of the concentration, said calibration curve generated from images of droplets captured and detected in the same way, said images of droplets corresponding to a plurality of colored solutions of known concentrations of said solute; and
   iv. generating numerical values corresponding to the solute concentration in the sample from said comparison.

2. The system of claim 1, wherein it is a computing device that is selected from the group consisting of a smartphone and a computing device with an internal camera.

3. A method for determining the concentration of a solute in a colored liquid solution, comprising the steps of:
   a. placing on a suitable surface and under appropriate conditions, a plurality of colored droplets of solutions having known concentrations of a solute and a droplet of the sample solution whose solute concentration is to be determined;
   b. capturing, under appropriate conditions, an image of said plurality of droplets and of said sample using a camera coupled to a computing device;
   c. entering said known concentrations values of said solute for each of said colored solutions into the memory of said computing device;
   d. processing, by executing a computer application in said computing device, the values of the obtained images, both of said plurality of colored droplets of solutions having known concentrations of said solute, as well as the droplet of the sample whose concentration is to be determined, performing in said computing device the following operations:
  i. recognizing and detecting, in any position of a captured image, a droplet of a colored liquid sample whose solute concentration is to be determined;
  ii. obtaining numerical values related to the color of said recognized and detected image of said droplet of the sample whose solute concentration is to be determined;
  iii. comparing said obtained numerical values to a calibration curve of said numerical value as a function of the concentration, said calibration curve generated from images of droplets captured and detected in the same way, said images of droplets corresponding to a plurality of colored solutions of known concentrations of said solute; and
  iv. generating numerical values corresponding to the solute concentration in the sample from said comparison; and
e. watching in the screen of said computing device the value of the concentration of said solute in said sample calculated by means of the execution of said computer application.

4. The method of claim 3, wherein said appropriate surface for the placement of the droplets is a uniform surface, having a horizontal position and a contrasting color with respect to the color of the colored solutions.

5. The method of claim 4, wherein the color of said surface for the placement of the droplets is white.

6. The method of claim 3, wherein said appropriate conditions for the placement of the plurality of droplets of colored solutions having known concentrations of said solute and of the droplet of the sample whose concentration is to be determined are:
  three or more droplets of said colored solutions having known concentrations of said solute, having a volume in the range from 15 µL to 100 µL; and
  at least one droplet of the sample whose concentration is to be determined, having a similar volume to the droplets of colored solutions having known concentrations of said solute.

7. The method of claim 3, wherein said appropriate conditions for the capture of the images of the plurality of colored droplets of solutions having known concentrations of said solute and of the droplet of the sample whose concentration is to be determined are:
  an angle and a distance with respect to the surface in which the droplets are placed that allows the capture of a single image including all the droplets on said surface; and
  a uniform illumination for all the droplets on said surface, which may be both, a natural light source or an artificial light source.

8. The method of claim 3, wherein for calculating the value of the concentration of said solute of said sample, the computer application performs the following:
  i. recognizing each droplet in at least one previously captured and detected image, both the plurality of droplets of colored solutions having known concentrations of said solute as well as the droplet of the solution whose concentration is to be determined;
  ii. pre-processing said previously captured and detected image in a pixel matrix by means of an appropriate method for eliminating the noise from said image;
  iii. transforming said pixel matrix from the RGB color space to an appropriate color space for isolating the sample from the rest of the image;
  iv. post-processing said previously captured image by selecting the pixel blocks that represent a droplet on said matrix;
  v. removing the pixel blocks having a size lower than the 50% of the block having the greatest size;
  vi. generating a histogram of the color value of the pixels to provide the most repeated color in every droplet;
  vii generating a calibration plot of color as a function of the concentration of the droplets of colored solutions having known concentrations of said solute from said histogram; and
  viii. calculating the concentration of said solute in the droplet of the sample whose concentration is to be determined.

9. The method of claim 8, wherein said pre-processing of said previously captured and detected image comprises:
  i. obtaining an approximate area of said droplets;
  ii. detecting the area of said droplets in said pixel matrix in the RGB color space to 16 or 24 bits; and
  iii. applying a gaussian interpolation filter to said obtained images of said droplets.

10. The method of claim 8, wherein said post-processing of the previously captured image that selects the pixel blocks representing a droplet on the pixel matrix comprises:
  i. removing the pixels whose colors do not correspond to the main colors recognized in every droplet; and
  ii. detecting and storing in the memory the pixel blocks on the pixel matrix.

* * * * *